United States Patent [19]

Wagner et al.

[11] Patent Number: 4,591,569

[45] Date of Patent: May 27, 1986

[54] HOMOGENEOUS FLUORESCENT TRIIODOTHYRONINE UPTAKE TEST

[75] Inventors: Daniel B. Wagner, Raleigh; Luther W. Dasher, Durham, both of N.C.

[73] Assignee: Becton Dickinson & Company, Paramus, N.J.

[21] Appl. No.: 599,143

[22] Filed: Apr. 11, 1984

[51] Int. Cl.$^4$ .................. G01N 33/53; G01N 33/557; G01N 33/542

[52] U.S. Cl. ..................... 436/500; 436/517; 436/537; 436/800; 436/815; 436/817

[58] Field of Search .............. 436/500, 517, 800, 537, 436/815, 817

[56] References Cited

U.S. PATENT DOCUMENTS

| | | | |
|---|---|---|---|
| 4,272,505 | 6/1981 | Smith | 436/500 |
| 4,329,461 | 5/1982 | Khanna et al. | 436/500 |
| 4,358,604 | 9/1982 | Albarella et al. | 436/500 |
| 4,476,228 | 10/1984 | Huchzermeier et al. | 436/500 |
| 4,476,229 | 10/1984 | Fino et al. | 436/500 |
| 4,489,165 | 12/1984 | Wagner et al. | 436/500 |

FOREIGN PATENT DOCUMENTS

| | | | |
|---|---|---|---|
| 15695 | 9/1980 | European Pat. Off. | 436/800 |
| 2111476 | 7/1983 | United Kingdom | 436/800 |

OTHER PUBLICATIONS

Smith, Febs Lett. 77(1) 25-27 (1977).

*Primary Examiner*—Christine M. Nucker
*Attorney, Agent, or Firm*—Elliot M. Olstein; John N. Bain

[57] ABSTRACT

Homogeneous assay for determining thyroid binding capacity by use of a fluorescent $T_3$ tracer, such as $T_3$ coupled to a fluorescein dye through a radical derived from L-lysine.

7 Claims, No Drawings

HOMOGENEOUS FLUORESCENT TRIIODOTHYRONINE UPTAKE TEST

This invention relates to an assay, and more particularly to a $T_3$ uptake assay.

$T_3$ uptake tests have been used to measure the unsaturated binding capacity of serum proteins, and in particular, thyroxine binding globulin (TBG).

In a typical $T_3$ uptake test, a $T_3$ tracer, generally a radioiodinated form of $T_3$, is added to a serum sample in an amount sufficient to saturate the binding sites on the TBG in the serum. Subsequently, the labeled $T_3$ which is not bound by the serum is separated from the bound labeled $T_3$, and the amount of unbound $T_3$ tracer is measured to determine the percent of $T_3$ tracer which is bound by the serum. The amount of $T_3$ tracer which is bound by the serum is compared with the percentage of $T_3$ tracer bound in a reference sample so as to determine whether or not there is an increase or decrease in the thyroid binding capacity of the serum sample. In particular, the ratio of the percent binding of the $T_3$ tracer in the serum sample to the percent binding of $T_3$ tracer in a reference sample is multiplied by the percent uptake of a normal pool sample to provide the $T_3$ uptake of the serum sample.

In the conventional $T_3$ uptake assays, there is a need to separate the bound $T_3$ tracer from the unbound $T_3$ tracer. Accordingly, there is a need for a homogeneous $T_3$ uptake test which eliminates the necessity for separating the bound and free portions.

In accordance with one aspect of the present invention, there is provided a $T_3$ uptake test wherein a $T_3$ tracer comprised of a fluorescent material linked to $T_3$ is contacted with a sample to be assayed, and the fluorescence of the sample is then determined as a measure of $T_3$ uptake.

More particularly, in accordance with the present invention, Applicant has found that by using certain $T_3$ tracers there can be provided a homogeneous $T_3$ uptake test in that binding of such tracers to TBG regenerates some of the quenched fluorescence of the tracer in proportion to the concentration of binding sites, whereby a measure of the fluorescence provides a homogeneous fluorescent $T_3$ uptake test.

More particularly, the tracers which are employed in the $T_3$ uptake assay of the present invention are tracers produced by linking or conjugating $T_3$ to a fluorescein dye through a spacer radical derived from either (1) an amino acid having a carboxyl and/or amino substituent group in addition to the amino and carboxyl groups which are characteristic of the amino acid, or (2) a dicarboxylic acid. The tracers which are preferably employed in the present invention are represented by the following structural formulas:

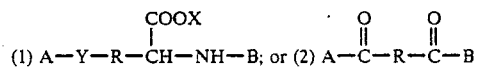

wherein
X is hydrogen, an amine salt, ammonium or a metal, such as an alkali metal or alkaline earth metal
Y is —NH— or

and
R is a substituted or unsubstituted divalent hydrocarbon radical having from 1 (preferably at least 2) to 13 carbon atoms, and when R is substituted the substituent group is preferably a hydrophylic group such as hydroxyl, carboxyl, amino or thio, and wherein in compound (1) —R— and —CH— may be linked to form a carbocyclic chain; and
A is one of $T_3$ or a fluorescein dye, preferably a fluorescein dye, and B is the other of a fluorescein dye and $T_3$, preferably $T_3$.

In the tracer, wherein Y is an amino group, the amino group is conjugated to the fluorescein dye through a suitable substituent group; for example, carboxyl (amide or peptide linkage); isothiocyanate (thiourea linkage); and when Y is carbonyl, the carbonyl group is most generally conjugated to the fluorescein dye through an amino substituent group (amide or peptide linkage). $T_3$ is conjugated through either its amino or carboxyl group depending on the functional group available in the spacer compound used for conjugating the fluorescent compound to $T_3$.

Of particular interest as fluorescein dyes, there may be mentioned: fluorescein isothiocyanate, fluorescein amine, 5(6)-carboxylfluorescein and dichlorotriazinylaminofluorescein.

In producing a tracer in accordance with the present invention, R preferably has no more than 6 carbon atoms, and is most preferably alkylene. In addition, Y is preferably amino. Particularly preferred results are obtained when the spacer radical is derived from L-lysine. When deriving the spacer radical from L-lysine, the amino group adjacent to the carboxyl group is preferably conjugated to $T_3$, and the remaining amino group is preferably conjugated to the fluorescein dye.

The conjugate comprised of fluorescein dye linked to $T_3$ through a spacer radical of the type hereinabove described, may be produced by linking or conjugating the spacer radical to both the fluorescein dye and $T_3$ by any one of a wide variety of procedures, which are known in the art, for producing linkages of the type hereinabove described.

Thus, for example, peptide linkages may be formed by an active ester technique. Similarly, if appropriate, substituent groups may be blocked in order to provide the linkage of the desired substituent group on the amino acid. Since these procedures are well known in the art, no further details in this respect are deemed necessary for a complete understanding of the present invention. In most cases, the amino acid radical is initially conjugated to the fluorescein dye, followed by conjugation of the chromogen-amino acid conjugate to $T_3$. It is to be understood, however, that such procedure may also be reversed.

A preferred tracer has the following structural formula:

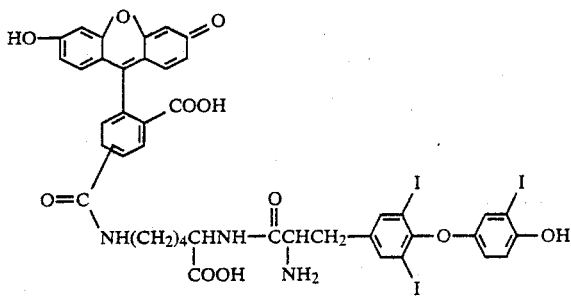

In the $T_3$ uptake assay of the present invention, the reference sample or a serum sample is admixed with the $T_3$ tracer, and subsequently the fluorescence of the sample is determined. In addition, a blank reference or test serum sample is also run.

The fluorescence of the tracer is enhanced by binding with TBG in the serum or reference sample, and as a result, an increase in fluorescence indicates an increase in the binding capacity of the sample.

The $T_3$ uptake of the serum sample is determined by comparing the fluorescence of the serum sample with the fluorescence of a reference sample. For example, the percent of $T_3$ uptake may be determined as follows:

$$\% \ T_3 \ \text{Uptake} = \frac{\text{Fluorescence of Test}_{Ref} - \text{Fluor. of Blank}_{Ref}}{\text{Fluorescence of Test}_{Unk} - \text{Fluor. of Blank}_{Unk}} \times T_3 \ \text{Uptake Value of Reference}$$

In accordance with the assay of the present invention, the increase in fluorescence is proportional to the concentration of TBG binding sites, with the concentration of TBG binding sites being inversely proportional to $T_4$ output in serum. Thus, an increase in the $T_3$ uptake as hereinabove calculated is representative of a decrease in the $T_4$ output (hypothyroid sera). Similarly, a decrease in the $T_3$ uptake is representative of an increase in $T_4$ output (hyperthyroid sera).

The invention will be further described with respect to the following examples; however, the scope of the invention is not to be limited thereby:

EXAMPLE 1

CARBOXYFLUORESCEIN-LYSINE-3,3',5-TRIIODO-L-THYRONINE CONJUGATE

Five ml of thionyl chloride were added to a solution of 1.0 g 5(6)-carboxyfluorescein-ε-lysyl-amide in 50 ml of anhydrous MeOH, and the solution was cooled in a dry-ice acetone bath. After stirring for 5 min, the cooling bath was removed, and the reaction mixture was kept at 40°–50° C. for 2 hr. The solid which was left upon evaporation was chromatographed on a silica gel colum eluting with chloroform:MeOH 4:1 to yield 0.51 g of the methyl ester.

A solution of 3,3'-5-triiodo-N-trifluoroacetyl thyronine (2.2 g) in 30 ml of anhydrous pyridine was treated with 0.60 g of dicyclohexylcarbodiimide, followed by 0.50 g of the methyl ester of 5(6)-carboxyfluorescein-ε-lysylamide. The reaction mixture was kept at room temperature for 2 hr, and the solid which was left upon evaporation of the volatiles was partitioned between ethyl acetate and brine, acidified with 10% citric acid.

The organic layer was washed with water (to pH 4.0) and with brine. The solid dicyclohexylurea was removed by filtration, and the ethyl acetate solution was evaporated to dryness, affording the crude, protected conjugate.

The crude conjugate was dissolved in a 1 M solution of morpholine in MeOH (50 ml), and the reaction mixture was left at room temperature overnight. Ten ml of 2 n NaOH solution were added, and the dark orange solution was left at room temperature for 6 hr. The solid which was left on evaporation of the volatiles was partitioned between ethyl acetate and 10% citric acid solution. The organic layer was washed with brine, dried, and evaporated to dryness. The residue was partially purified by column chromatography (silica gel, gradient chloroform:MeOH 1:1 to pure MeOH) to give the carboxyfluorescein-lysine-3,3',5-triiodo-L-thyronine conjugate.

EXAMPLE 2

T-3 UPTAKE - FLUORESCENCE ENHANCEMENT ASSAY

The protocol for quantitation of T-3 uptake by fluorescence enhancement is described below:

REAGENTS (1) Barbital buffer, 0.075 M, pH 8.6
(2) Tracer of Example 1 diluted in barbital buffer
(3) T-3 uptake reference serum

PROTOCOL

For each sample, the following tubes were prepared:

| BLANK | TEST |
|---|---|
| 50 ul reference or test serum | 50 ul reference or test serum |
| 750 ul barbital buffer | 750 ul fluorescent T-3 |

The above tubes were mixed and incubation was 5 minutes at room temperature.

FLUORESCENCE MEASUREMENT

Samples were read on fluorometer at the following settings:

Excitation wavelength=488 nm, slit 10

Emission wavelength=515 nm, slit 15

CALCULATION $$\% \ T_3 \ \text{Uptake} = \frac{\text{Fluorescence of Test}_{Ref} - \text{Fluor. of Blank}_{Ref}}{\text{Fluorescence of Test}_{Unk} - \text{Fluor. of Blank}_{Unk}} \times T_3 \ \text{Uptake Value of Reference}$$

RESULTS

Fluorescence enhancement ranged from 1.90 for hyperthyroid sera to 2.12 for euthyroid serum to 2.59 for hypothyroid sera. Serum background was on the average 30% of the gross fluorescence of the test samples.

Seventy-eight (78) serum samples were run by this method and correlated with T-3 $I^{125}$ uptake assay. Results were as follows:

slope = 0.788 y-intercept = 10.99 correlation coefficient = 0.912

The present invention is particularly advantageous in that it is possible to effect a $T_3$ uptake test without separating the bound and free portions of the tracer; i.e., the assay is a homogeneous uptake assay. Moreover, such an assay is accomplished in a serum sample by fluorescent enhancement, without adverse serum interference, as shown by the correlation between the assay of the invention and the known radioassay for $T_3$ uptake.

Numerous modifications and variations of the present invention are possible in light of the above teachings and, therefore, within the scope of the appended claims, the invention may be practiced otherwise than as particularly described.

What is claimed is:

1. In an assay for determining the thyroid hormone binding capacity of a serum sample, the improvement comprising:

mixing a $T_3$ tracer with a serum sample, and determining the $T_3$ uptake of the sample by fluorescent enhancement without separating bound and unbound portions of $T_3$ tracer; said $T_3$ tracer comprising a compound having the following structural formula:

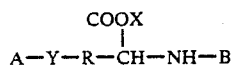

wherein

X is selected from the group consisting of hydrogen, amine salt, ammonium and metal cations Y is —NH— or

and

R is selected from the group consisting of substituted and unsubstituted divalent hydrocarbon radicals having from 1 to 13 carbon atoms, and wherein —R—and —CH— may be linked to form a carbocyclic chain; and A is one of a $T_3$ radical and a fluorescein dye and B is the other of a $T_3$ radical and a fluorescein dye.

2. The assay of claim 1 wherein R is an alkylene radical having 4 carbon atoms and Y is —NH—.

3. The assay of claim 1 wherein the tracer is

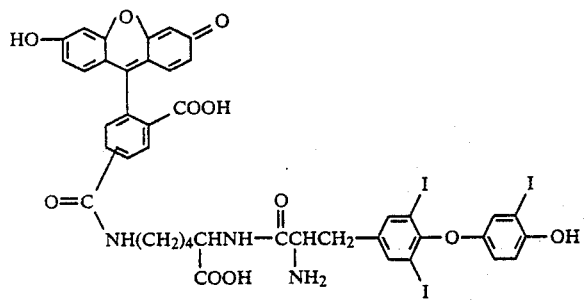

4. The assay of claim 1 wherein R is alkylene.
5. The assay of claim 4 wherein Y is —NH—.
6. The assay of claim 7 wherein enhancement of fluorescence is determined by use of a fluorimeter.
7. The assay of claim 4 wherein enhancement of fluorescence is determined by use of a fluorimeter.

* * * * *